(12) United States Patent
Kidwell

(10) Patent No.: US 6,443,892 B1
(45) Date of Patent: Sep. 3, 2002

(54) SWEAT COLLECTING DEVICE AND METHODS FOR USE AND DETECTION OF TAMPERING

(75) Inventor: David A. Kidwell, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 2 days.

(21) Appl. No.: 09/671,167

(22) Filed: Sep. 28, 2000

(51) Int. Cl.⁷ .............................. A61B 5/00; A61B 5/05
(52) U.S. Cl. ........................................ 600/362; 600/346
(58) Field of Search .................. 600/345, 346, 600/362, 300, 301, 347, 348, 367, 365, 363, 361, 357, 309

(56) References Cited

U.S. PATENT DOCUMENTS

| | | |
|---|---|---|
| 4,329,999 A | 5/1982 | Phillips |
| 4,444,193 A * | 4/1984 | Fogt et al. .................. 600/362 |
| 4,706,676 A | 11/1987 | Peck |
| 4,756,314 A | 7/1988 | Eckenhoff et al. |
| 4,819,645 A * | 4/1989 | Peck .......................... 600/362 |
| 4,821,733 A | 4/1989 | Peck |
| 4,909,256 A * | 3/1990 | Peck .......................... 600/362 |
| 4,957,108 A | 9/1990 | Schoendorfer et al. |
| 4,960,467 A | 10/1990 | Peck |
| 5,203,327 A | 4/1993 | Schoendorfer et al. |
| 5,441,048 A | 8/1995 | Schoendorfer |
| 5,522,967 A | 6/1996 | Shet |
| 5,676,144 A * | 10/1997 | Schoendorfer .............. 600/362 |
| 5,817,011 A * | 10/1998 | Schoendorfer .............. 600/362 |
| 5,899,856 A | 5/1999 | Schoendorfer et al. |
| 5,907,037 A | 5/1999 | Gujral et al. |
| 6,042,543 A * | 3/2000 | Warwick et al. ............ 600/362 |
| 6,063,029 A * | 5/2000 | Saita et al. .................. 600/309 |

OTHER PUBLICATIONS

D.A. Kidwell, J.C. Holland, and S. Athanaselis, Testing for drugs of abuse in saliva and sweat, J. Chromatog. B, 713 (1998) 111–135.

D.E.C. Cole et al, Use of new sample–collection device (Macroduct™) in anion analysis of human sweat, Clin. Chem. 32 (1986) pp. 1375–1378.

M. Phillips et al, Long–term sweat collection using salt–impregnated pads, J. Invest. Dermatol. 68 (1977) pp. 221–224.

M. Phillips, An improved adhesive patch for long–term collection of sweat, Biomater. Med. Dev. Artif. Org., 8 (1980) pp. 13–21.

M. Phillips et al, A sweat–patch test for alcohol consumption: evaluation in continuous and episodic drinkers, Alcohol Clin. Exp. Res., 4 (1980) pp. 391–395.

J. Levinsky et al., Drug Deposition in adipose tissue and skin: evidence for an alternative source of positive sweat patches, Forensic Science International 110 (2000) 35–46.

* cited by examiner

Primary Examiner—Kevin Shaver
Assistant Examiner—Navin Natnithithadha
(74) Attorney, Agent, or Firm—John J. Karasek; Joseph T. Grunkemeyer (57) ABSTRACT

The invention is useful for providing sweat collecting devices for the detection of chemicals or biochemicals in the perspiration of a living subject while reducing drug contamination from without (external sources), and for detecting tampering of the sweat collection device. The invention also provides a method for using the sweat collecting device which reduces and identifies prior chemical or biochemical contamination on the skin of the tested subject.

22 Claims, 4 Drawing Sheets

| ABSORBENT PAD MATERIAL | NG/PATCH COCAINE | NG/PATCH HEROIN | NG/PATCH AMPHETAMINE | NG/PATCH METHAMPHETAMINE | NG/PATCH MDMA |
|---|---|---|---|---|---|
| WHATMAN 3 MM CHROMATO-GRAPHY PAPER | 27 | 42 | 21 | 22 | 17 |
| ANSYS DIAGNOSTICS, INC. GLASS FIBER DISCS EMBEDDED WITH BONDED SILICA, WHERE THE BONDED SILICA IS BONDED WITH A STRONG CATION EXCHANGER | 106 | 32 | 51 | 60 | 93 |

FIG. 6

SWEAT COLLECTING DEVICE AND METHODS FOR USE AND DETECTION OF TAMPERING

BACKGROUND OF THE INVENTION

1. Field of the Invention

The invention relates generally to devices for the detection of chemicals and biochemicals in perspiration, methods for detecting chemicals and biochemicals using sweat collection devices, and methods for detecting tampering of sweat collection devices.

2. Description of the Related Art

Ingested drugs have long been known to appear in perspiration, which is defined here as including active perspiration such as that induced by exercise and heat, passive (insensible) perspiration, sebum, and other bodily excretions that appear on the skin surface, see D. A. Kidwell, J. C. Holland, and S. Athanaselis, Testing for drugs of abuse in saliva and sweat, J. Chromatog. B, 713 (1998) 111–135, incorporated herein by reference. A number of sweat collection devices have been developed to facilitate drug detection, including those described by Schoendorfer, et al. in U.S. Pat. No. 4,957,108 issued Sep. 18, 1990; Schoendorfer, et al. in U.S. Pat. No. 5,076,273 issued Dec. 31, 1991; Schoendorfer, et al. in U.S. Pat. No. 5,203,327 issued Apr. 20, 1993; Schoendorfer in U.S. Pat. No. 5,438,984 issued Aug. 8, 1995; Scheondorfer in U.S. Pat. No. 5,441,048 issued Aug. 15, 1995; Schoendorfer, et al. in U.S. Pat. No. 5,445,147 issued Aug. 29, 1995; Schoendorfer in U.S. Pat. No. 5,465,713 issued Nov. 14, 1995; Schoendorfer in U.S. Pat. No. 5,638,815 issued Jun. 17, 1997; Schoendorfer in U.S. Pat. No. 5,676,144 issued Oct. 14, 1997; Schoendorfer in U.S. Pat. No. 5,817,011 issued Oct. 6, 1998; Schoendorfer in U.S. Pat. No. 5,817,012 issued Oct. 6, 1998; Schoendorfer, et al in U.S. Pat. No. 5,899,856 issued May 4, 1999; Schoendorfer in U.S. Pat. No. 5,944,662 issued Aug. 31, 1999; D. E. C. Cole et al, Use of a new sample-collection device (Macroduct™) in anion analysis of human sweat, Clin. Chem. 32 (1986) pages 1375–1378; M. Phillips et al, Long-term sweat collection using salt-impregnated pads, J. Invest. Dermatol. 68 (1977) pages 221–224; M. Phillips, An improved adhesive patch for long-term collection of sweat, Biomater. Med. Dev. Artif. Org., 8 (1980) pages 13–21; C. C. Peck, Dermal substance collection device, U.S. Pat. No. 4,706,676, issued Nov. 17,1987; C. C. Peck, Dermal substance collection device, U.S. Pat. No. 4,960,467, issued Oct. 2, 1990; C. C. Peck, Dermal substance collection device, U.S. Pat. No. 4,819,645, issued Apr. 11, 1989; J. B. Eckenhoff et al, Sweat collection patch, U.S. Pat. No. 4,756,314, issued Jul. 12, 1988; and M. Phillips et al, A sweat-patch test for alcohol consumption: evaluation in continuous and episodic drinkers, Alcohol Clin. Exp. Res., 4 (1980) pages 391–395, all incorporated herein by reference.

Generally, sweat collection devices sandwich an absorbent pad between the skin and an outer membrane using a tamper-evident adhesive backing on the membrane. Careful preparation of the skin prior to application of the patch helps reduce the possibility of bacterial growth and previous skin contamination. Non-occlusive membranes allow water vapor to pass through the membrane, which increases comfort for the wearer and allows longer-term wear.

One currently commercially available device has combined the non-occlusive membrane with a cellulose collection pad to produce a sweat collection patch. Sweat patches have found wide application in the criminal justice system due to perceived advantages including user friendliness, non-invasiveness, easily observed placement and removal of the sweat patch, detectable adulteration attempts including punctures by needles and attempts to remove the device and either replace it with a new device or the same device, long drug-use detection interval during the wearing of approximately one week, and potential to identify unique metabolites. In addition, there are reports that the sweat patch may either deter or cause individuals to be more forthcoming about drug use.

Two reported features of the commercially available sweat patch are first, that the patch appears to protect the skin from contamination by the external environment after being applied, and second, that the skin is cleansed before application of the patch, potentially removing previously deposited drugs. The manufacturer of one commercially available patch states that "passive exposure to ambient drugs of abuse during the wear period is not detected by conventional toxicological analysis of post-wear patches" see Product Package Insert Part # P00020 Revision: A. PHARMCHEK™ Drugs of Abuse Patch For Collection of Cocaine and Cocaine Metabolite, Amphetamines, Opiates, Cannabinoid and Cannabinoid Metabolites, and Phencyclidine (PCP) Through the Skin. PharmChem Laboratories, Inc. Menlo Park, Calif. 1999.

An article by P. Kintz, Drug Testing in Addicts: a Comparison between Urine, Sweat, and Hair, Therapeutic Drug Monitoring, 18 (1996), incorporated herein by reference, suggested that nonvolatile substances from the environment cannot penetrate the transparent film, a semipermeable membrane over the pad that allows oxygen, water, and carbon dioxide to pass through the patch, leaving the skin underneath healthy. Further, in M. Burns et al, Monitoring Drug Use with a Sweat Patch: an Experiment with Cocaine, J. Anal. Tox., 19(January/February) (1994) 41–48, incorporated herein by reference, researchers suggested that larger nonvolatile molecules that cannot pass the polyurethane layer remain trapped on the collection pad. Additionally, V. Spiehler et al, Enzyme Immunoassay Validation for Qualitative Detection of Cocaine in Sweat, Clinical Chemistry, 42(1) (1996) 34–38 states that the transparent film portion of the patch allows oxygen, carbon dioxide, and water vapor to escape but prevents the escape of nonvolatile constituents present in sweat. An additional account by G. Skopp, et al, Preliminary Practical Findings on Drug Monitoring by a Transcutaneous Collection Device, J. Forensic Sci., 41(6) (1996) 933–937, stated that molecules larger than vapor-phase isopropanol are excluded by the molecular pore structure (~2 nm) of the plastic membrane. Skopp, et al. used the dye rhodamine B to study the permeability of the sweat patch's polyurethane membrane from Contamination From WithOut, (CFWO), where drugs external to the patch can penetrate the membrane. No CFWO was observed with rhodamine B. However, Skopp et al. used a hydrophilic dye, with both amine and carboxylic acid functional groups. The state of hydration of the inner pad is not reported. If the inner pad was dry, transport of molecules would be reduced and give a false impression of impermeability. Cone, et al., in Sweat Testing for Heroin, Cocaine, and Metabolites, J. Anal. Toxicol. 18 (1994) pages 298–305, incorporated herein by reference, explored CFWO by exposing subjects wearing skin patches to cocaine vapor. They observed some unexpectedly, high concentrations of cocaine (greater than 200 ng per patch), but dismissed them as laboratory handling error "because other patches collected from the same subject under similar conditions were determined to be negative". Furthermore, subjects wore light clothing to cover the patches and were not actively sweating, factors which are predicted to lessen CFWO.

The sweat patch is becoming increasingly used in the U.S. criminal justice system to monitor drug use during pretrial and probationary release. Recently, offices of the U.S. Federal Public Defender have described cases where individuals under supervised pretrial or probationary release have had their sweat patch test positive while denying drug use in a credible manner. Cases include individuals with negative urine test results and positive sweat patch results, or close contact with a drug-contaminated environment. Several of these cases involved individuals identified as methamphetamine positive, who denied vehemently any methamphetamine use, some even while admitting they used other illegal drugs. In at least one instance, consecutive 48-hour urine specimens which covered the length of wear of the patch, tested negative while the patch tested positive. A common thread running through these cases was that the individuals were in environments where profuse sweating was commonplace and, frequently, tested positive for drugs with which they had a prior use history and possible environmental contamination.

In an article by Kidwell and Smith, Susceptibility of PharmChek™ Drugs of Abuse Patch to Environmental Contamination, NRL Memorandum Report NRL/MR/6170-99-8414, Nov. 3, 1999 and Forensics Science International 2910 (2000) pages 1–18 (attached, now published with new pagination at Forensics Science International 116 (2–3), 89–106, Feb. 15, 2001), both incorporated herein by reference, the authors conclude that both Contamination From WithIn (CFWI), where skin is contaminated with drugs before application of the sweat patch, and Contamination From WithOut (CFWO), where drugs external to the patch can penetrate the membrane, can occur in the present design for the sweat patches, leading to possible false positive test results.

CFWI is distinct from the process where drugs permeate the skin in areas not covered by the patch, enter the blood stream, and are re-excreted in sweat into the patch. Except in extreme cases of external contamination, this is unlikely to occur because, generally speaking, drugs do not enter the bloodstream through skin in high concentrations, see Kidwell and Smith, NRL Memorandum NRL/MR/6170-99-8414, page 13 and Forensics Science International 2910 (2000) section 3.2, page 10. For CFWI to be observed, only a source of drugs, a plausible transfer mechanism to the skin, and binding of the drugs to the skin need occur. Because most individuals tested for drug use by the patch are previous drug users, their environment is more likely to be contaminated with drugs, increasing the likelihood that their skin will contact drugs from prior drug using episodes. Because the skin is cleansed using 70% isopropanol swabs before application of the patch, it was thought that prior drug exposures of the skin should not affect the results. D. A. Kidwell et al. Cocaine Detection in a University Population by Hair Analysis and Skin Swab Testing, Forensic Sci. Int., 84 (1997) pages 75–86, incorporated herein by reference, found that 70% isopropanol does not remove all the drug deposited on the skin, and that alcohol combined with a mild acid provided a better solvent for drug removal. A mild acid is one that is suitable for use on human subjects. The people most likely to be tested by the sweat patch are also the most likely to be externally contaminated.

Figure 1:
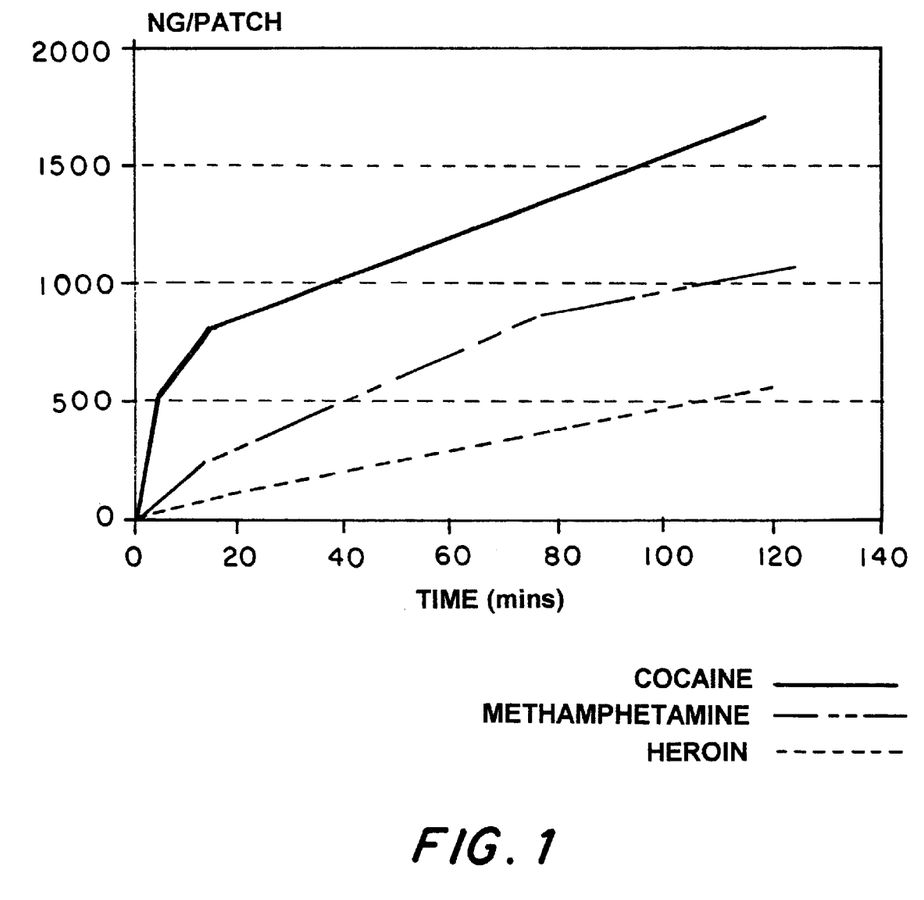
FIG. 1 is a chart showing how rapidly drugs penetrate the membrane from the outside when placed in slightly basic media such as sodium bicarbonate (pH 8.3) showing the diffusion of drugs placed on the outside of the patches.

Kidwell and Smith, Susceptibility of PharmChek™ Drugs of Abuse Patch to Environmental Contamination, NRL Memorandum Report NRL/MR/6170-99-8414 and Forensics Science International 2910 (2000) pages 1–18, also Found that when the membrane of a commercially available sweat patch was tested for the passage of externally applied materials (CFWO), drugs in the uncharged state rapidly penetrated the membrane of the patch, but those in the charged state were greatly slowed. This occurs because the drugs in the uncharged state are soluble in the membrane, while drugs in the charged state are not. Thus when aqueous solutions are in contact with both sides of the membrane, drugs are able to diffuse through. This occurs fastest when the external aqueous solution containing the drugs is alkaline and the internal aqueous solution in the absorbent pad is acidic. Since sweat is normally neutral or acidic, diffusion of drugs through the membrane can be promoted. In basic media, detectable concentrations of cocaine, methamphetamine and heroin were observed at the earliest collection time after drugs were placed on the outside of the membrane, at approximately 30 seconds. Drug concentrations increased over a two hour time course, when the amounts detected represented 5–17% of the drugs deposited on the surface of the sweat patch. FIG. 1 depicts the rapid penetration of drugs through the membrane from the outside when placed in slightly basic media such as sodium bicarbonate (ph 8.3).

Additionally, Kidwell et al, in Susceptibility of PharmChek™ Drugs of Abuse Patch to Environmental Contamination, NRL Memorandum Report NRL/MR/6170-99-8414 pages 12–15, and Cocaine Detection in a University Population by Hair Analysis, Forensic Sci. Int., 84 (1997) pages 75–86 demonstrated that drugs externally applied to human skin bound readily. Drugs deposited on the skin of drug-free volunteers several days prior to the application of the sweat patch were not completely removed by normal hygiene or the cleaning procedures recommended before application of the sweat patch. Even six days of normal hygiene did not remove all drugs from externally contaminated skin and resulted in positive sweat patch tests.

Figure 2:
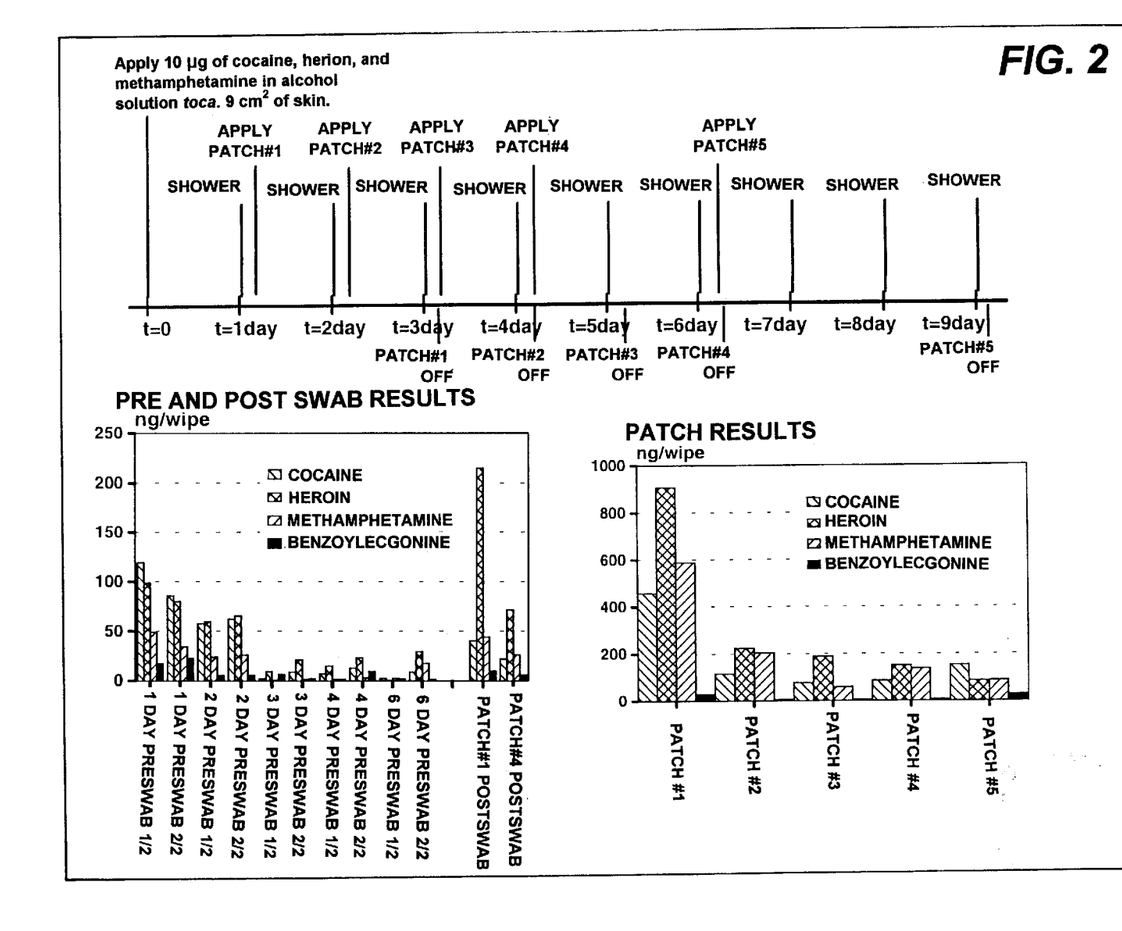
FIG. 2 depicts an experiment where drugs were spiked on five areas of skin and patches were applied at various times, days after the drug application, and with varying amounts of normal hygiene. All sweat patches showed CFWI. Sweat patch concentrations of all drugs applied to the skin generally decreased over time, with a few data points showing variability from this trend. Even when the patch was applied seven days after skin contamination with drugs, cocaine, BE, heroin, and methamphetamine were deposited in the pad. The top graph is a summary of the experiment and the bottom two bar charts summarize the analysis results.
Figure 3:
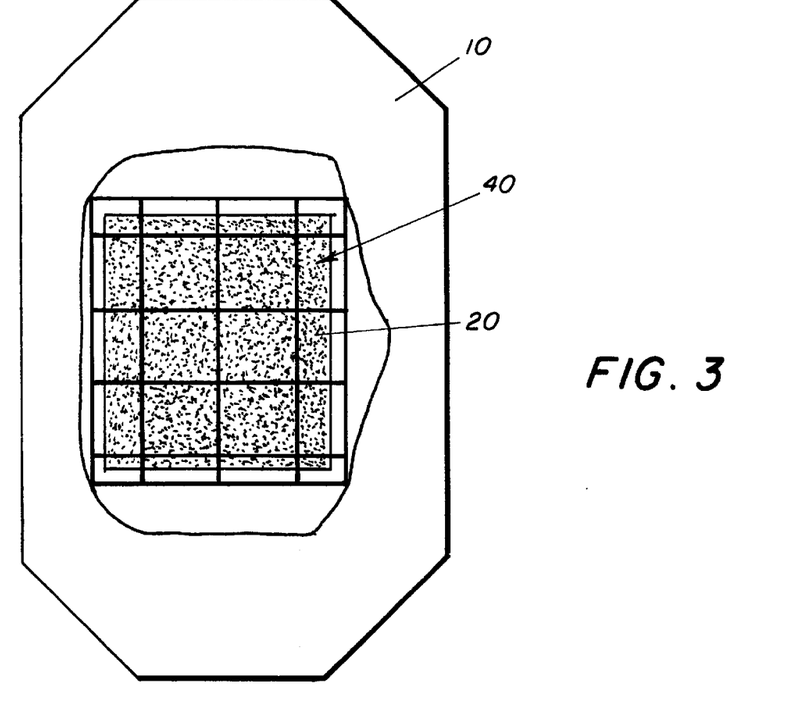
FIG. 3 is a schematic representation of a one-membrane device. The device has a membrane layer (10) and an absorptive pad layer (40) separated by an air gap (20).
Figure 4:
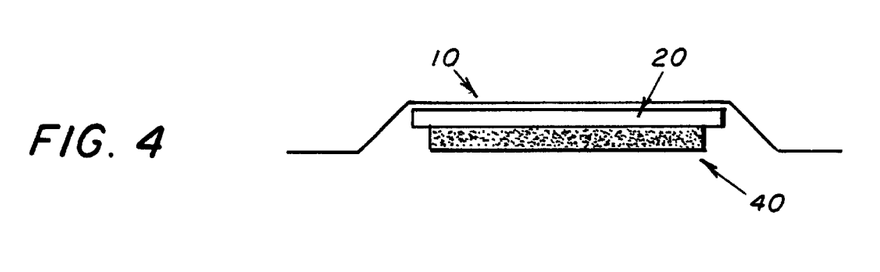
FIG. 4 is a cross section of the one membrane device of FIG. 3. The device has a membrane (10) and an absorptive pad layer (40) separated by an air gap (20).
Figure 5:
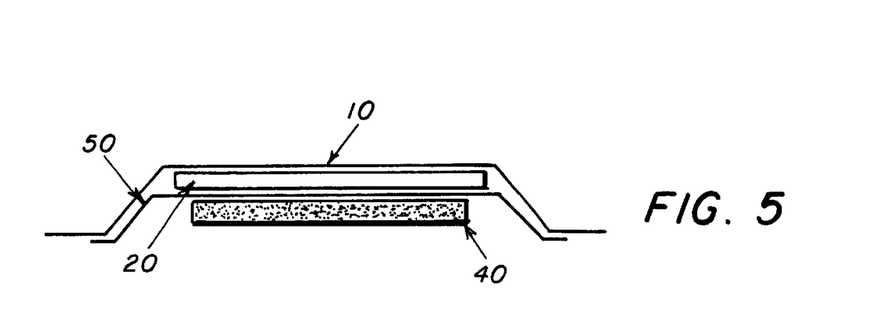
FIG. 5 is a cross-section of a two membrane device. The device has a first membrane layer (10) and a second membrane layer (50) separated by an air gap (20). An absorbent pad (40) is located under the second membrane layer (50).

FIG. 2 depicts an experiment by Kidwell and Smith where drugs were placed on five areas of skin and patches were applied at various times, days after the drug application, and with varying amounts of normal hygiene. All sweat patches showed CFWI. Sweat patch concentrations of all drugs applied to the skin generally decreased over time, with a few data points showing variability from this trend. Even when the patch was applied seven days after skin contamination with drugs, cocaine, BE, heroin, and methamphetamine were deposited in the pad. Sources of variability may include the extent of normal hygienic cleansing, the placement of the sweat patch over the contaminated area, and the effects of exercise on active sweating. Drug concentrations in skin swabs taken just prior to patch applications (prepatch swabs) tapered off with time after contamination. By day 6, only one pre-patch swab contained significant quantities of drugs. Concentrations of drugs decreased between the post-swab after patch #1. (Several post-patch alcohol swabs were lost.) These results show that it is possible for an individual to be externally contaminated with these drugs on one day, perform normal hygienic washing for at least six days, cleanse the skin twice with 70% isopropyl alcohol swabs, and still test positive for cocaine, heroin, and methamphetamine in the sweat patch.

Potential sources of drug contamination for CFWI and CFWO are plentiful. Cocaine in particular and also methamphetamine, are found on paper currency, see J. C. Hudson, Analysis of currency for cocaine contamination, Can. Soc. For. Sci., 22, 203, 1989, J. Oyler et al., Cocaine Contamination of United States Paper Currency, J. Anal.Toxicol., 20 (1996) 213–216, and A. Negrusz et al., Detection of Cocaine on Various Denominations of United States Currency, J. Forensic Sci., 43 (1998) 626–629. Although drugs on currency are hard to transfer to the skin, they can transfer if the skin is moist, see D. A. Kidwell et al., Testing for Elicit Drugs via Sweat and Saliva Analysis: Application to the Detection of Body Packers, in the Proccedings of the 1999 ONDCP International Technology Symposium, Mar. 8–10, 1999, Washington, D.C., pp. 21–15. This indicates the ease that drugs can spread through the general environment. Likewise, individuals whose environments are predicted to contain drug contamination show higher levels of drugs on their skin, see A. Tracqui et al., The Detection of Opiate Drugs in Non Traditional Specimens (Clothing): a Report of Ten Cases, J. Forensic Sci., 40 (1995) 263–265. Touching the patch with one's hand is a natural reaction to materials on the body. Also, some court officers consider it a violation if the patch peels off. Thus, intentionally pressing on the patch to keep adhered to the skin could also transfer drugs to the surface from the hands. Alternatively, wearing a close fining undershirt, contaminated with as little as microgram quantities of these drugs, (above the patch), and sweating could transfer drugs to the surface of the patch. The laboratory studies show that the potential for external contamination of skin (CFWI) as well as contamination of the patch membrane (CFWO) can occur and generate false positive results. The exact percentage and degree of drug contamination in specific environments is generally not known. To the extent that drugs must pass through the human body to produce metabolites, metabolites can increase the reliability of a positive result. Unfortunately, for cocaine the major metabolite, benzoylecgonine, is present to a small extent in street-grade cocaine (see J. F. Casale et al., A Chromatographic Impurity Signature Profile Analysis for Cocaine using Capillary Gas-Chromatography, J. Forensic Sci, 36 (1991) pages 1312–1330) and appears to be produced by cocaine degradation on the skin. In contrast, amphetamine is the major metabolite of methamphetamine and is less likely present in illicit methamphetamine preparations. Nevertheless, amphetamine is sometimes sold as methamphetamine and thus may contaminate the environment.

Contamination may also come from the sweat of prior use. Because the individual being tested may still reside in the same location, wear clothing, or contact other drug users, this contact may put that individual in proximity to metabolites generated from other people or at a prior time. Contact with metabolites may be ruled out based on the circumstances of the subject's environment but contact with the parent drug could still be a possibility. Thus, the studies show that the potential for external contamination of skin (CFWI) as well as contamination of the patch membrane (CFWO) can occur and generate false positive results.

The current scheme to detect tampering in the commercially available patch according to the product literature is to conduct a visual inspection of the patch before it is removed to determine if it is undisturbed and if the membrane has any holes. A single pinprick is very difficult to detect with a visual inspection, yet can still allow the introduction of foreign substances through pressure injection. Base would degrade cocaine to ecgonine, a compound not normally detectable by immunoassays or by gas chromatography and mass spectrography, and thus allow a cocaine user to escape detection. Heroin and methamphetamine would not be degraded to undetectable products and consequently users of these drugs would not generate false negatives.

The current sweat patches do not adequately prevent CFWO. Additionally, the current methods for using the sweat patch do not adequately indicate the possibility of CFWI. Further, the current sweat patches and methods for their use do not adequately detect tampering. Therefore, there is a strong need for sweat patch devices and methods of using sweat patch devices hat reduce CFWO and detect and reduce CFWI thus producing more accurate and reliable results, and also allowing for easier detection of tampering.

SUMMARY OF THE INVENTION

Accordingly, it is an object of the present invention to provide devices and methods for collecting chemicals and biochemicals in perspiration for analysis whereby CFWO is reduced.

It is an object of the present invention to provide devices and methods for collecting chemicals and biochemicals in perspiration whereby CFWI is reduced and/or detected.

It is a further object of the present invention to provide devices and methods for collecting chemicals and biochemicals in perspiration for analysis in which tampering is more easily detected.

Additional objects and advantages of the invention will be set forth in part in the description which follows, and, in part, will be obvious from the description, or may be learned by practice of the invention.

The foregoing objects of the present invention are achieved by providing a device and method for collecting drugs and other biochemicals or chemicals in perspiration to provide for increased accuracy of test results by decreasing CFWO, decreasing and detecting CFWI, and more easily detecting tampering.

The present invention comprises a multilayer device, minimally including a membrane which allows water vapor and air to escape, an absorbent pad for collecting the perspiration, and an air gap between the membrane and the absorbent pad. Substances may be incorporated into the device to allow for easy detection of tampering. Additional layers may be present in the device.

Alternatively, the device can include a second membrane layer between the absorbent pad and the first membrane layer, with an air gap between the first membrane layer and the absorbent pad layer, either above or below the second membrane layer. Two membranes would reduce the chance of flooding of the air gap with sweat during periods of heavy exercise. Flooding in a one membrane device could allow contact of the interior surface of the membrane with the sweat and potentially permit CFWO. Substances may be incorporated into the device to allow for easy detection of tampering.

Another aspect of the invention is a method for detecting CFWI, having the steps of cleansing the skin with a swab, and saving the used cleansing swab for later analysis.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Sweat patches were constructed using a membrane layer, which allows air and water vapor to escape from the sweat patch, and an absorbent filter paper pad used for absorbing perspiration. The sweat patch contained an air gap to prevent the membrane from contacting the absorbent pad. The purpose of the air gap is to separate the membrane from the absorbent pad, thereby prevent movement of liquid between the membrane and the absorbent pad and preventing liquid in the absorbent pad from contacting the membrane. Preventing such liquid contact can greatly reduce diffusion of CFWO into the pad. The air gap was maintained by a screen between the absorbent pad and the membrane. The patches were wetted with artificial sweat internally and externally, then placed in a drug vapor chamber. Specifically, the patch was constructed using 3 M Tegaderm™ dressings (National Drug Code (NDC) 8333-1624-05) as the membrane and a Whatman #3 filter paper pad. The patch was then exposed to drug vapors. The patch reduced CFWO for cocaine by 98% as compared to a similarly constructed patch without the air gap and screen.

In an alternative design the permeable membrane does not cover the entire air gap. The remaining portion of the patch can be covered by a non-permeable membrane, as only enough permeable membrane is needed to allow for water evaporation from the patch. This design could decrease the cost of manufacturing the patch.

An alternative sweat patch design would provide a second membrane between the first membrane and the absorbent pad. An air gap separates the absorbent pad and the first membrane, either above or below the second membrane. The two membrane design would reduce the chance of flooding where the air gap fills with sweat during heavy exercise. Flooding could allow for contact of the interior surface of the membrane in a single membrane device with the sweat and potentially allow external contaminants into the patch. Preferably, the air gap is between the first membrane and the second membrane.

An alternative design of the sweat patch would provide a second membrane between the first membrane and the absorbent pad, the two membranes being separated by a second absorbent pad to absorb CFWO, which may be tested if the results of the sweat patch test are questioned. The presence of a large amount of drugs in the second absorbent pad (used for absorbing CFWO) may be grounds to reject a positive finding as some of these drugs could leak into the first absorbent pad used to absorb perspiration.

An alternative design for the device contains a spacer that maintains the air gap.

Alternatively the spacer that maintains the air gap is composed of a material that does not absorb water and allows air and water vapor to pass yet maintains an air gap between the membrane and the absorbent pad.

Alternatively, the material of the spacer is screen, mesh, fiberglass, woven material or other fibrous material that maintains an air gap between the membrane and absorbent pad.

An alternative design for the sweat patches contains substances for the detection of tampering. At least one compound acting as an internal standard is incorporated into the patch and tested in the laboratory when the patch itself is tested. These substances are easily incorporated into the device by placing a small quantity of the substance on the absorbent pad used for collecting perspiration or on the spacer. The quantity of the substance is the amount of substance corresponding to the midrange of the cut-off values used for assaying that particular drug. For example, if the cut-off value for cocaine is 25 ng per patch, then incorporate 50–100 ng per patch of the substance into the patch. The cut-off value is the quantity of drug that the testing laboratory determines indicates a positive test result. The substance should behave in a similar manner as the chemicals or biochemicals being tested for, under such conditions as are present when tampering with the device is attempted, for example when the pH is changed in the patch, an oxidant is added to the patch, or light and heat are applied to the patch An alternative design for the sweat patches contains substances for the detection of tampering. A substance such as a drug homolog could be tested in the laboratory at the same time the patch was being tested for the chemical and biochemical substances. These homologs are easily incorporated into the device by placing a small quantity of the homolog on the absorbent pad used for collecting perspiration or on the spacer. The quantity of the homolog is the amount of homolog corresponding to the midrange of the cut-off values used for assaying that particular homolog. If the homolog was intact, then no tampering would have occurred. Methyl-p-methylbenzoyl ecgonine is an example of a drug homolog for cocaine.

An alternative design for the sweat patches contains substances for the visual detection of tampering. A substance such as a masked pH indicator such as acetylated bromocresol purple (BCP) is incorporated into the patch. If BCP is acetylated with a carboxylic acid, the acetylated BCP is a light yellow. Upon cleavage with base, the acetylated BCP returns to BCP which is purple above pH6. If the sweat patch has been tampered with by injection of a foreign substance, the color of the patch would be altered. The amount of indicating substance to be incorporated could vary to produce a level of color indication detectable to the human eye. Foreign substances frequently used to tamper with these devices are basic materials which degrade certain drugs of abuse.

An alternative design for the sweat patches contains substances for the visual detection of tampering A substance such as an oxidation reagent can be tested for by incorporation of a number of calorimetric dyes. ABTS (2,2'-azinobis (3-ethylbenzothiazoline-6-sulfonic acid) or Tetramethylbenzidine (TMB) are examples of oxidation reagents that are useful for this purpose. Foreign substances frequently used to tamper with these devices are oxidants, which degrade certain drugs of abuse.

Alternatively, the substance for the detection of tampering with the device is incorporated into either the absorbent pad or the spacer of the device.

Figure 6:
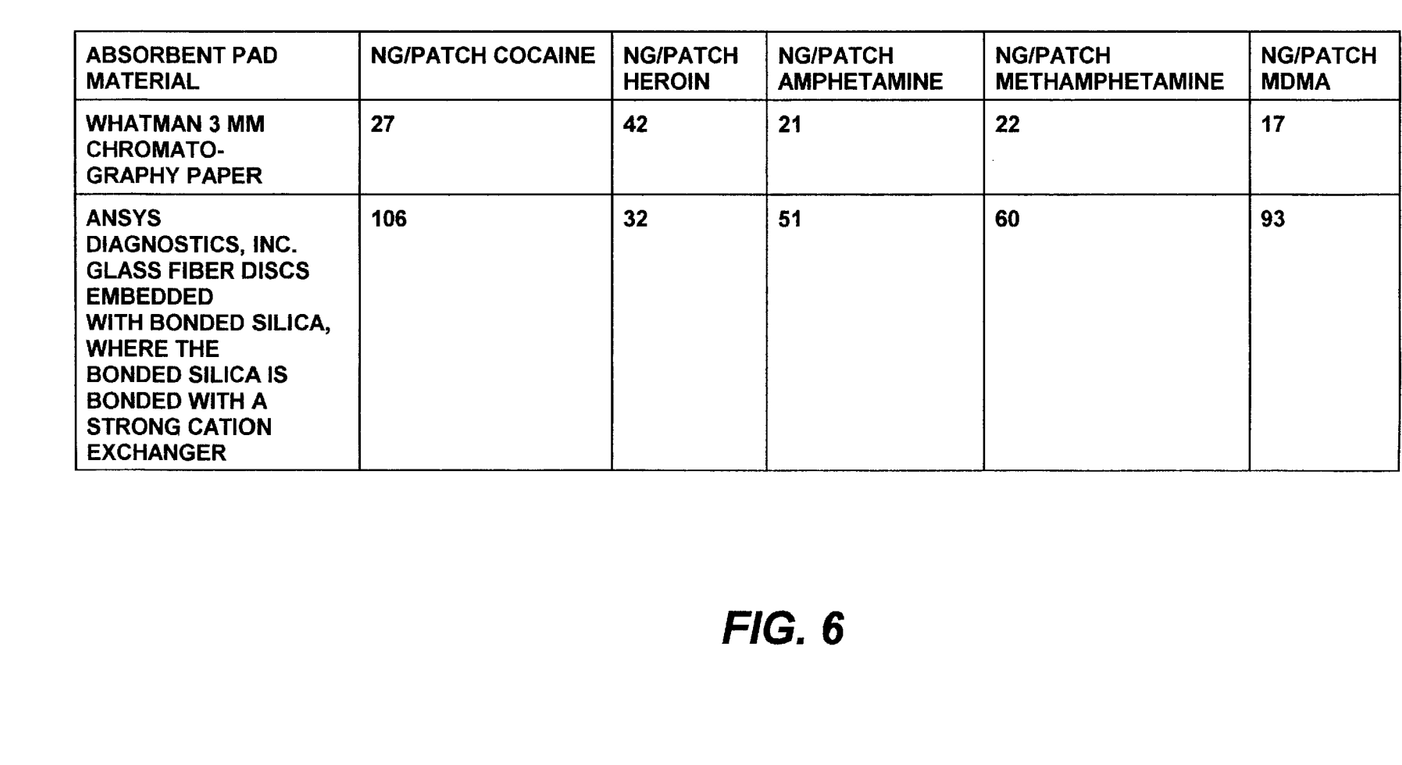
FIG. 6 is a table representing the results of an experiment wherein 5 $\mu$g of cocaine, heroin, amphetamine, methamphetamine, and MDMA were placed on the arms of human volunteers. The drugs were left overnight, followed by a hygienic shower in the morning, then the arms were cleansed twice with 70% isopropanol, and the sweat patches were applied. The patches either had absorptive pads made from Whatman 3 MM Chromatography paper or the Ansys cation exchanger described below in the preferred embodiments section. The patches were worn for 3 days, and the table of FIG. 6 presents the results.

Alternatively, the absorbent pad may contain at least one functionality which binds the substances being detected via ionic or hydrophobic bonds. The absorbent pad may be comprised of several layers, each with a separate functionality. Such functionalities may be synthetic small molecules or proteins, including antibodies, antibody fragments or receptors. An example is glass fiber discs embedded with bonded silica, where the bonded silica is bonded with a strong cation exchanger. Such material is produced by Ansys Diagnostics, Inc. An advantage of such an absorbent pad can be seen in FIG. 6. 5 μg of cocaine, heroin, amphetamine, methamphetamine, and MDMA were placed on the arms of human volunteers. The drugs were left overnight, followed by a hygienic shower in the morning, then the arms were cleansed twice with 70% isopropanol, and the sweat patches were applied. The patches either had absorptive pads made from Whatman 3 MM Chromatography paper or the Ansys cation exchanger described above. The patches were worn for 3 days, and the table of FIG. 6 presents the results. Further examples of absorbent pad materials would be sulfonated cellulose, as disclosed in Gujral, et al, U.S. Pat. No. 5,907,037, issued May 25, 1999, and Shet, U.S. Pat. No. 5,522,967, issued Jun. 4, 1996, both incorporated herein by reference, or phosphate derivatized cellulose (P-81) produced by Whatman as chromatography media.

The presence of CFWI on can be detected by a process comprising the steps of cleansing a portion of skin, preferably with a swab, saving the material removed from the skin, preferably in the used cleaning swab, analyzing the material to detect chemicals or biochemicals, applying a sweat collecting patch to the same potion of skin, analyzing the patch to detect the same chemicals or biochemicals, and determining the presence of CFWI by comparing the results of the analysis of the material to the results of the analysis of the patch. Preferably the swab contains an alcohol and, optionally a mild acid. Methods for analyzing the swab to detect chemicals or biochemicals are known in the art. Such methods include but are not limited to gas chromatography-mass spectroscopy. Determining the presence of CFWI can be performed by reference to amount of drugs typically removed with the swab. For example, it was found that a swab containing 70% isopropanol will remove at least 10% of the CFWI. Thus, a swab measurement that was more than 10% of the patch measurement would indicate the presence of CFWI.

Although a few embodiments of the present invention have been shown and described, it would be appreciated by those skilled in the art that changes may be made in these embodiments without departing from the principles and spirit of the invention, the scope of which is defined in the claims and their equivalents.

I claim:

1. A device for collecting chemicals or biochemicals in perspiration for later analysis comprising:

a membrane layer;

an absorbent pad layer for collecting perspiration located below said membrane layer; and an air gap between said membrane layer and said absorbent pad layer;

wherein said air gap separates said absorbent pad layer from said membrane layer to prevent movement of liquid between said absorbent pad layer and said membrane layer.

2. The device of claim 1, wherein said air gap is maintained by a spacer.

3. The device of claim 2 wherein the spacer is composed from a material that does not absorb water and allows air and water vapor to pass through said spacer, yet maintains said air gap between said membrane layer and said absorbent pad layer.

4. The device of claim 3 wherein said material is a fibrous material.

5. The device of claim 4 wherein said fibrous material is woven material.

6. The device of claim 3 wherein said material is screen or mesh.

7. A device for collecting chemicals or biochemicals in perspiration comprising:

a first membrane layer;

a second membrane layer located below said first membrane layer;

an absorbent pad layer under said second membrane layer for collecting perspiration; and an air gap between said first membrane layer and said absorbent pad layer;

wherein said air gap separates said absorbent pad layer from said first membrane layer to prevent movement of liquid between said absorbent pad layer and said first membrane layer.

8. The device of claim 7 wherein said air gap is maintained by a spacer.

9. The device of claim 8 wherein said spacer is composed of a material that does not absorb water and allows air and water vapor to pass though, yet maintains said air gap between the membrane and the absorbent pad.

10. The device of claim 9 wherein said material is a fibrous material.

11. The device of claim 9 wherein said material is woven material.

12. The device of claim 10 wherein said material is screen or mesh.

13. The device of claim 1 or 7 wherein at least one substance for the detection of tampering with said device is incorporated into said device.

14. The device of claim 13 wherein the substance for the detection of tampering with the device is a masked pH indicator.

15. The device of claim 13 wherein the substance for the detection of tampering with the device is an oxidation indicator.

16. The device of claim 13 wherein the substance for the detection of tampering with the device is a drug homolog.

17. The device of claim 7 wherein the air gap is between the firsts membrane and the second membrane.

18. A method for the determination of the presence of Contamination From Within (CWFI) on skin, comprising the steps of:

cleansing a portion of skin;

saving material removed from the said skin by said cleansing;

analyzing said material to detect chemicals or biochemicals; and applying a sweat collecting patch to said portion of skin;

analyzing said patch to detect said chemicals or biochemicals; and determining the presence of CFWI by comparing the results of the analysis of said material to the results of the analysis of said patch.

19. The method of claim 18 wherein said cleansing step is performed with a swab, and said saying step is performed by saving said swab.

20. The method of claim 19 wherein said swab contains an alcohol.

21. The method of claim 20 wherein said swab contains a mild acid.

22. A device for collecting chemicals or biochemicals in perspiration comprising;

a first membrane layer;

a second membrane layer located below said first membrane layer;

a first absorbent pad layer under said second membrane layer for collecting perspiration; and a second absorbent pad layer between the first membrane layer and the second membrane layer or absorbing CFWO.

* * * * *